United States Patent [19]

Palmer et al.

[11] Patent Number: 4,876,274

[45] Date of Patent: Oct. 24, 1989

[54] NEW CLASS OF PESTICIDES COMPRISING 1,4-BIS-SUBSTITUTED-2,6,7-TRIOXABICY-CLO(2.2.2)OCTANES

[75] Inventors: Christopher J. Palmer, Ipswich, England; John E. Casida, Berkeley, Calif.

[73] Assignee: The Regents of the University of California, Berkeley, Calif.

[21] Appl. No.: 902,083

[22] Filed: Aug. 27, 1986

Related U.S. Application Data

[63] Continuation of Ser. No. 692,818, Jan. 23, 1985, abandoned, which is a continuation-in-part of Ser. No. 575,843, Jan. 30, 1984, abandoned.

[51] Int. Cl.$^4$ ...................... A01N 43/32; A01N 51/00
[52] U.S. Cl. ..................................... 514/452; 514/149
[58] Field of Search .................. 514/450, 452, 149

[56] References Cited

PUBLICATIONS

JACS, 92, 2702–2709 (1970).
Chemical Abstracts 92: 174215p (1980).
Chemical Abstracts 90: 80705e (1979).
Chemical Abstracts 89: 36467j (1978).
Chemical Abstracts 85: 73049n (1976).
Chemical Abstracts 63: 16370d (1965).

Primary Examiner—Douglas W. Robinson
Attorney, Agent, or Firm—Nixon & Vanderhye

[57] ABSTRACT

A pesticidal composition comprising a compound having the formula R—C(CH$_2$O)$_3$C—X wherein R and X are each organic substituents and wherein the compound has an LD$_{50}$, in micrograms of compound per gram of body weight of a selected pest, of less than about 400 and/or an LD$_{50}$ in the presence of synergist of less than about 20 is disclosed along with its use in killing pests. Pesticidal activity has been found against a broad range of types of insects. The pesticidal activity of the composition is strongly enhanced by the use of a selected synergist.

20 Claims, No Drawings

NEW CLASS OF PESTICIDES COMPRISING 1,4-BIS-SUBSTITUTED-2,6,7-TRIOXABICY-CLO(2.2.2)OCTANES

ACKNOWLEDGEMENT OF GOVERNMENT SUPPORT

This invention was made with Government support under Grant No. ES00049 awarded by the National Institutes of Health. The Government has certain rights in this invention.

CROSS-REFERENCE

This is a continuation of application Ser. No. 692,818, filed Jan. 23, 1985, now abandoned, which in turn is a continuation-in-part of application Ser. No. 575,843, filed Jan. 30, 1984, now abandoned.

TECHNICAL FIELD

The present invention relates to a new class of pesticides which are 1,4-bis-substituted-2,6,7trioxabicyclo[2.2.2]octanes.

BACKGROUND OF THE INVENTION

Pesticides are chemicals which combat the attacks of various pests on crops, livestock, man and their environment. They include insecticides, fungicides, herbicides (or weed killers), nematicides, molluscicides, acaricides and parasiticides.

Many classes of compounds are known to exhibit pesticidal activity. Unfortunately, known pesticidal compositions may become less effective with time because of the development of resistance in the species against which they are used. Thus, there is a constant need for new types of pesticides.

An ideal pesticide has high effectiveness in controlling pests, and is biodegradable.

The present invention is concerned with providing pesticidal compositions having desirable properties such as those set forth above.

DISCLOSURE OF THE INVENTION

In accordance with an embodiment of the present invention, a pesticidal composition is set forth which comprises a compound having the formula $R-C(CH_2O)_3C-X$ wherein R and X are each organic substituents and wherein the compound has a pesticidal activity, as $LD_{50}$ in micrograms of the compound per gram of body weight of a selected insect, of no more than of about 400.

In accordance with another embodiment of the present invention, a pesticidal composition is set forth comprising a compound having the formula $R-C(CH_2O)_3C-X$ wherein R and X are each organic substituents along with a synergist for pesticidal activity, together having an $LD_{50}$ of no more than about 20 micrograms of the compound per gram of body weight.

In accordance with still another embodiment of the present invention a composition of matter is set forth comprising a compound having the formula $R-C(CH_2O)_3C-X$ wherein:

R=n-propyl, iso-propyl, n-butyl, s-butyl, tert-butyl, cyclopentyl, cyclohexyl, phenyl, 4-methylphenyl or nitro; and wherein X=vinyl, ethynyl, 1-bromoethyl, 1,2-dibromoethyl, cyclopropyl, s-butyl, cyclobutyl, neo-pentyl, cyclopentyl, n-hexyl, cyclohexyl, cycloheptyl, cyclohex-3-enyl, 1-bicyclo[2.2.1]heptyl, 2-bicyclo[2.2.1]heptyl, 5-bromo-2-furyl, 2chlorophenyl, 3-chlorophenyl, 4-chlorophenyl, 2-fluorophenyl, 4-fluorophenyl, 4-bromophenyl, 3,4-dichlorophenyl, 4-tert-butylphenyl, 3-phenoxyphenyl, 4-trifluoromethylphenyl, 4-azidophenyl, 4-nitrophenyl, 4-cyanophenyl, 4-methylsulfonylphenyl, 4-methylthiophenyl, 4-methoxyphenyl, 4-methylphenyl, 4-chloro-3-nitrophenyl, 3,4-methylenedioxyphenyl or 2,3,4,5,6-pentafluorophenyl.

Still another embodiment in accordance with the present invention is a compound having the formula $R-C(CH_2O)_3C-X$ wherein:

R=n-propyl, iso-propyl, n-butyl, s-butyl, tert-butyl, cyclopentyl, cyclohexyl or phenyl; and wherein X=ethynyl, cyclohexyl, cycloheptyl, cyclohex-3-enyl, 2-bicyclo[2.2.1]heptyl, 3-chlorophenyl, 4-chlorophenyl, 2-fluorophenyl, 4-fluorophenyl, 4-bromophenyl, 3,4-dichlorophenyl, 4-trifluoromethylphenyl, 4-azidophenyl, 4-nitrophenyl, 4-cyanophenyl, or 2,3,4,5,6-pentafluorophenyl.

In accordance with yet another embodiment of the present invention a composition of matter is set forth comprising a compound having the formula $R-C(CH_2O)_3C-X$ wherein:

X is 4-chlorophenyl and R is ethyl, n-propyl, i-propyl, n-butyl, s-butyl, t-butyl, cyclopentyl, cyclohexyl, phenyl, 4-methylphenyl, or nitro; or wherein X is cyclohexyl and R is cyclohexyl, ethyl or phenyl; or wherein R is cyclohexyl and X is phenyl, 4-fluorophenyl, 4-bromophenyl, 4-cyanophenyl, 3,4-dichlorophenyl, or cycloheptyl; or wherein R is t-butyl and X is 2-fluorophenyl, 2-chlorophenyl, 3-chlorophenyl, 4-fluorophenyl, 4-bromophenyl, 4-trifluoromethylphenyl, 4-nitrophenyl, 4-cyanophenyl, 4-azidophenyl, 4-t-butylphenyl, 3,4-dichlorophenyl, 2,3,4,5,6-pentafluorophenyl, n-pentyl, cyclohexyl, cycloheptyl, ethynyl, or benzyl; or wherein R is i-propyl and X is 3-phenoxyphenyl, 4-nitrophenyl, 4-methoxyphenyl, 4-methylphenyl, 2,3,4,5,6-pentafluorophenyl, s-butyl, neopentyl, n-hexyl, cyclopropyl, cyclobutyl, cyclopentyl, cyclohexyl, cycloheptyl, vinyl, ethynyl, 1-bromoethyl or 1,2-dibromoethyl; or wherein R is n-propyl and X is 4-methylsulfonylphenyl, 4-methylthiophenyl, 4-chloro-3-nitrophenyl, 3,4-methylenedioxyphenyl, 1-bicyclo[2.2.1]heptyl, 2-bicyclo[2.2.1]heptyl, cyclohex-3enyl, or 5-bromo-2-furyl; or wherein R is phenyl and X is phenyl or 4-fluorophenyl.

Another embodiment yet of the invention is a compound having the formula $R-C(CH_2O)_3C-X$ wherein:

X is 4-chlorophenyl and R is n-propyl, i-propyl, n-butyl, s-butyl, t-butyl, cyclopentyl, cyclohexyl, or phenyl; or wherein X is cyclohexyl and R is cyclohexyl, or phenyl; or wherein R is cyclohexyl and X is phenyl, 4-fluorophenyl, 4-bromophenyl, 4-cyanophenyl, 3,4-dichlorophenyl, or cycloheptyl; or wherein R is t-butyl and X is 2-fluorophenyl, 3-chlorophenyl, 4-fluorophenyl, 4-bromophenyl, 4-trifluoromethylphenyl, 4-nitrophenyl, 4-cyanophenyl, 4-azidophenyl, 3,4-dichlorophenyl, 2,3,4,5,6-pentafluorophenyl, n-pentyl, cyclohexyl, cycloheptyl, or ethynyl; or wherein R is i-propyl and X is 4-nitrophenyl, cyclohexyl or cycloheptyl; or wherein R is n-propyl and X is 2-bicyclo[2.2.1]heptyl or cyclohex-3-enyl.

In accordance with other embodiments of the present invention, the insecticidal compositions previously mentioned are used to kill selected pests.

The preferred pesticidal compositions of the present invention have acceptably high pesticidal activity, particularly when used with a synergist, and are biodegradable. They have been shown to exhibit significant pesticidal activity against such diverse insects as the common housefly, American and German cockroaches, aphid, milkweed bug and mosquito larva.

BEST MODE FOR CARRYING OUT THE INVENTION

In accordance with the present invention, a compound is provided having the formula $R-C(CH_2O)_3-C-X$ wherein R and X are each organic substituents at the 4- and 1- positions respectively in the compound. It has been shown that this class of compounds includes a number of chemicals which exhibit significant pesticidal activity. It has also been found that some compounds of this general formula do not exhibit such pesticidal activity, even when used in combination with a synergist. Tables 1-5, which follow, show the relative effectiveness for control of houseflies and American cockroaches of a number of compounds of the general formula set forth above, both alone and with the synergist piperonyl butoxide (PB). The abbreviations used are as follows: Me-methyl, Et-ethyl, Pr-propyl, Bu-butyl, Pen-pentyl, Hex-hexyl, Hept-heptyl, Ph-phenyl, n-normal, i-iso, s-secondary, t-tertiary, and c-cyclo.

The pesticides of the present invention exhibit a pesticidal activity, as $LD_{50}$ in micrograms of the pesticide per gram of body weight of a selected pest, of no more than about 400. For example, such an activity has been shown as an insecticide against *Musca domestica* as is discussed below. The pesticides of the present invention alternatively or additionally exhibit a pesticidal activity, as $LD_{50}$ in micrograms of the pesticide per gram of body weight of a selected pest, of no more than about 60 and more preferably of no more than about 20. Such an activity has been shown as an insecticide against *Musca domestica* as is discussed below.

The use of synergists with pesticides is well known and is discussed in detail in the publication "Mixed-Function Oxidase Involvement in the Biochemistry of Insecticide Synergists", J. E. Casida, *J. Agric. Food Chem.*, 18, 753-772 (1970). The compounds of the present invention become even more effective with synergists which function to inhibit microsomal cytochrome P-450 oxidases that detoxify the pesticide thereby allowing a longer period for pesticidal action and consequently higher toxicity. Such synergists include those listed in the above publication plus other synertgists which function in the manner stated.

The compositions of the present invention may be used in combination with an inert carrier that serves as a diluent or vehicle for the active pesticides. For example, the toxicant may be dissolved in petroleum hydrocarbons, tetrahydrofuran, acetone, cellosolves or any other suitable inert carrier prior to use. Alternatively, the toxicant may be adsorbed on a solid inert carrier such as talc, clay, finely ground silica or the like.

Contacting of pests with the pesticides of the present invention can be by any effective and convenient method, including any of the various methods of contacting well known in the art and used for delivering prior art pesticides to insects or other pests. For example, the pesticide may be utilized as a spray, an aerosol, dust or granules, or may be impregnated into or coated onto a structure with which the insect or other pests may come into contact, may be mixed with or impregnated into bait, may be incorporated with a substance or structure which slowly releases it in an area normally frequented by the pest or may be incorporated with and/or into other formulations which are directed into contact with the pest or placed where the pest will be likely to contact such formulations. The pesticides may be mixed with an inert carrier to facilitate delivery of the pesticides to the pests.

The toxicity to houseflies is dependent on both the R and X substiuents as shown in Table 1 giving the first definitive evidence of effectiveness. The 1,4-bis-substituted-2,6,7-trioxabicyclo[2.2.2]octanes were tested both alone and along with PB. Further refined evaluations of these and many other compounds revealed certain preferred R and X substituents (Tables 2-4).

The effect of the R-substituent on the effectiveness of the toxicants both alone and along with PB on houseflies is presented in Table 2.

TABLE 1

Housefly Control by 1,4-bis-Substituted-2,6,7-trioxabicyclo[2.2.2]octanes Alone and With the Synergist Piperonyl Butoxide

| R—C(CH$_2$O)$_3$C—X | | Compound number | $LD_{50}$, μg/g | |
|---|---|---|---|---|
| R | X | | With Synergist | Alone |
| t-Bu | 4-BrPh | 25 | 0.4 | 4 |
| c-Hex | 4-ClPh | 8 | 0.4 | 37 |
| t-Bu | 3,4-Cl$_2$Ph | 38 | 1 | 5 |
| c-Hex | c-Hex | 13 | 1 | 13 |
| t-Bu | 4-ClPh | 6 | 1 | 15 |
| n-Pr | 4-ClPh | 2 | 2 | 10 |
| t-Bu | c-Hex | 60 | 2 | 40 |
| c-Hex | 4-FPh | 24 | 2 | >500 |
| t-Bu | 4-FPh | 23 | 3 | >500 |
| t-Bu | 3-ClPh | 21 | 4 | 125 |
| n-Bu | 4-ClPh | 4 | 4 | 23 |
| Ph | c-Hex | 14 | 5 | 225 |
| c-Hex | Ph | 18 | 5 | >500 |
| Ph | 4-ClPh | 9 | 7 | 400* |
| i-Pr | c-Hex | 59 | 8 | >500 |
| i-Pr | 4-ClPh | 3 | 12 | 100 |
| t-Bu | Ph | 17 | 23 | >500 |
| t-Bu | 2-FPh | 19 | 25 | >500 |
| t-Bu | n-Bu | 51 | 50 | 450 |
| n-Pr | Ph | 15 | 60 | >500 |
| n-Pr | n-Bu | 69 | 100 | >500 |
| t-Bu | Ethynyl | 65 | 125 | 150 |
| t-Bu | Benzyl | 68 | 125 | >500 |
| i-Pr | Ethynyl | 64 | 125 | >500 |
| Et | c-Hex | 12 | 225 | >500 |
| Ph | 4-FPh | 45 | 225 | >500 |
| Ph | Ph | 44 | 250 | >500 |
| t-Bu | n-Pr | 49 | 375 | >500 |
| 4-MePh | 4-ClPh | 10 | >150 | >150 |
| t-Bu | H | 46 | >500 | >500 |
| t-Bu | Me | 47 | >500 | >500 |
| t-Bu | Et | 48 | >500 | >500 |
| t-Bu | i-Pr | 50 | >500 | >500 |
| t-Bu | 4-t-BuPh | 37 | >500 | >500 |
| i-Pr | Vinyl | 63 | >500 | >500 |
| i-Pr | 3-PhOPh | 22 | >500 | >500 |
| i-Pr | 1-BrEt | 66 | >500 | >500 |
| i-Pr | 1,2-Br$_2$Et | 67 | >500 | >500 |
| NO$_2$ | 4-ClPh | 11 | >500 | >500 |

*Value based on suspension in acetone with only partial solution.

TABLE 2

Effect of R-Substituent on the Topical Toxicity to Houseflies of 1-(4-Chlorophenyl)- 2,6,7-trioxabicyclo[2.2.2]octanes and Three 1-Cyclohexly Analogs

| R-substituent | compound number | LD$_{50}$ µg/g, with PB (and alone) |
|---|---|---|
| Et[a] | 1 | 105 (>500) |
| n-Pr | 2 | 2.5 (23) |
| i-Pr | 3 | 8.3 (140) |
| n-Bu | 4 | 3.5 (17) |
| s-Bu | 5 | 2.7 (58) |
| t-Bu | 6 | 1.5 (10) |
| c-Pen | 7 | 2.0 (21) |
| c-Hex[a] | 8 | 0.53 (10) |
| Ph[a] | 9 | 2.5 (41) |
| 4-MePh | 10 | >500 (>500) |
| NO$_2$ | 11 | >500 (>500) |

[a]Compound numbers and LD$_{50}$ [µg/g with PB (and alone)] in the 1-c-Hex series are: (12) 4-Et 350 (>500); (13) 4-c-Hex 0.63 (8.5); (14) 4-Ph 7.0 (375).

TABLE 3

Effect of Substitution on 1-Phenyl Group (X) on the Topical Toxicity to Houseflies of 4-Alkyl-2,6,7-trioxabicyclo[2.2.2]octanes and Two 4-Phenyl Analogs

| substituent on 1-phenyl group (X) | compound number | | | | LD$_{50}$, µg/g, with PB(and alone) | | | |
|---|---|---|---|---|---|---|---|---|
| | 4-n-Pr | 4-i-Pr | 4-t-Bu | 4-c-Hex | 4-n-Pr | 4-i-Pr | 4-t-Bu | 4-c-Hex |
| H[a] | 15 | 16 | 17 | 18 | 90 (>500) | 90 (>500) | 23 (>500) | 13 (>500) |
| 2-F | | | 19 | | | 30 (>500) | | |
| 2-Cl | | | 20 | | | 105 (>500) | | |
| 3-Cl | | | 21 | | | 6.3 (375) | | |
| 3-PhO | | 22 | | | | >500 (>500) | | |
| 4-F[a] | | | 23 | 24 | | | 5.5 (>500) | 1.9 (>500) |
| 4-Cl | 2 | 3 | 6 | 8 | 2.5 (23) | 8.3 (140) | 1.5 (10) | 0.53 (10) |
| 4-Br | | | 25 | 26 | | | 0.83 (3.5) | 0.25 (6.5) |
| 4-CF$_3$ | | | 27 | | | | 53 (>500) | |
| 4-NO$_2$ | | 28 | 29 | | | 11 (>500) | 5.0 (>500) | |
| 4-CN | | | 30 | 31 | | | 0.23 (4.8) | 0.65 (115) |
| 4-N$_3$ | | | 32 | | | | 13 (160) | |
| 4-MeSO$_2$ | 33 | | | | >500 (>500) | | | |
| 4-MeS | 34 | | | | >500 (>500) | | | |
| 4-MeO | | 35 | | | | 265 (>500) | | |
| 4-Me | | 36 | | | | 250 (>500) | | |
| 4-t-Bu | | | 37 | | | | >500 (>500) | |
| 3,4-Cl$_2$ | | | 38 | 39 | | | 0.88 (4.3) | 2.5 (30) |
| 3-NO$_2$,4-Cl | 40 | | | | >500 (>500) | | | |
| 3,4-OCH$_2$O | 41 | | | | >500 (>500) | | | |
| 2,3,4,5,6-F$_5$ | | 42 | 43 | | | 135 (>500) | 18 (240) | |

[a]Compound numbers and LD$_{50}$ values [µg/g, with PB(and alone)] in the 4-Ph series are (44) H 325 (>500) and (45) 4-F 250 (>500).

TABLE 4

Effect of 1-Substituent (X) on the Topical Toxicity to Houseflies of 4-Isopropyl- and 4-t-Butyl-2,6,7-trioxabicyclo[2.2.2]octanes and Five 4-n-Propyl and two 4-Cyclohexyl Analogs

| 1-substituent (X) | compound no. | | LD$_{50}$, µg/g, with PB (and alone) | |
|---|---|---|---|---|
| | 4-i-Pr | 4-t-Bu | 4-i-Pr | 4-t-Bu |
| H | | 46 | | >500 (>500) |
| Me | | 47 | | >500 (>500) |
| Et | | 48 | | >500 (>500) |
| n-Pr | | 49 | | 425 (>500) |
| i-Pr | | 50 | | >500 (>500) |
| n-Bu[a] | | 51 | | 55 (450) |
| s-Bu | 52 | | >500 (>500) | |
| n-Pen | | 53 | | 33 (365) |
| neo-Pen | 54 | | >500 (>500) | |
| n-Hex | 55 | | 160 (>500) | |
| C-Pr | 56 | | >500 (>500) | |
| c-Bu | 57 | | >500 (>500) | |
| c-Pen | 58 | | 500 (>500) | |
| c-Hex[a] | 59 | 60 | 14 (>500) | 3.5 (165) |
| c-Hept[a] | 61 | 62 | 8.5 (300) | 2.0 (44) |
| Vinyl | 63 | | >500 (>500) | |
| Ethynyl | 64 | 65 | 325 (>500) | 90 (175) |
| 1-BrEt | 66 | | >500 (>500) | |
| 1,2-Br$_2$Et | 67 | | >500 (>500) | |
| Benzyl | 68 | | 210 (>500) | |

[a]Compound numbers and LD$_{50}$ values [µg/g with PB (and alone) are: in the 4-n-Pr series (69) 1-n-Bu 155 (>500), (70) 1-(1-bicyclo[2.2.1]heptyl) 125 (>500), (71) 1-(2-bicyclo[2.2.1]heptyl) 10 (160), (72) 1-(cyclohex-3-enyl) 19 (110) and (73) 1-(5-bromo-2-furyl) 68 (500: in the 4-c-Hex series (13) 1-c-Hex 0.63 (8.5) and (74) 1-c-Hept 2.0 (13).

The effect of substitution on the 1-phenyl group (X) on the topical toxicity to houseflies of 4-alkyl-2,6,7-trioxabicyclo[2.2.2]octanes and two 4-phenyl analogs was tested. Table 3 presents the results of the testing.

The effect of the X substituent on the topical toxicity to houseflies of 4-isopropyl- and of 4-t-butyl-2,6,7-trioxabicyclo[2.2.2]octanes and five 4-n-propyl and two 4-cyclohexyl analogs was tested. Table 4 presents the results of the testing.

The toxicity to American cockroaches of topically-applied 1,4-bis-substituted-2,6,7-trioxabicyclo[2.2.2]octanes was tested. Table 5 presents the results of the testing.

TABLE 5

Toxicity to American Cockroaches of Topically-Applied 1,4-bis-Substituted-2,6,7-trioxabicyclo[2.2.2]octanes

| R—C(CH$_2$O)$_3$C—X | | compound number | LD$_{50}$ µg/g, with PB |
|---|---|---|---|
| R | X | | |
| n-Pr | 4-ClPh | 2 | 2 |
| n-Bu | 4-ClPh | 4 | 3 |
| t-Bu | 4-ClPh | 6 | 1[a] |
| c-Pen | 4-ClPh | 7 | 2 |
| c-Hex | 4-ClPh | 8 | 1[a] |
| Ph | 4-ClPh | 9 | 7 |
| c-Hex | c-Hex | 13 | >8 |
| t-Bu | 4-BrPh | 25 | 1[a] |
| c-Hex | 4-BrPh | 26 | 1 |
| t-Bu | 3,4-Cl$_2$Ph | 38 | >10 |

TABLE 5-continued

Toxicity to American Cockroaches of Topically-Applied 1,4-bis-Substituted-2,6,7-trioxabicyclo[2.2.2]octanes

| R—C(CH$_2$O)$_3$C—X | | compound | |
|---|---|---|---|
| R | X | number | LD$_{50}$ μg/g, with PB |
| t-Bu | c-Hex | 60 | 2[a] |

[a] At least 20-fold synergism by PB.

The above data indicate that compounds of the formula R—C(CH$_2$O)$_3$C—X are often effective pesticides. R or X may be alkyl, alkenyl, alkynyl, cycloalkyl or cycloalkenyl, each of which may be normal, branched or substituted, or may be aryl or substituted aryl or heterocycle. When R is a normal or branched alkyl, a cycloalkyl or aryl, useful compounds result. Preferably, the number of carbon atoms in R is three to ten. More preferably R is n-propyl, t-butyl, cyclohexyl, cyclopentyl, i-propyl, n-butyl, s-butyl or phenyl. X is preferably cycloalkyl or substituted cycloalkyl or cycloalkenyl having six to ten carbon atoms, normal alkyl, alkynyl, substituted alkyl or substituted alkynyl, or substituted phenyl. Effective pesticides result with cyclohexyl and cycloheptyl substituents. Other useful substituents include n-penyl, cyclohex-3-enyl and 2-bicyclo[2.2.1]-heptyl. The substituents on the phenyl group, when the phenyl group is the group X, are preferably halogens, cyano, nitro or azido groups.

PROCEDURES OF SYNTHESIS

Methods for making compounds of the general formula set out above can be found in the following publications: "Structure-Toxicity Relationships of 1-Substituted-4-alkyl-2,6,7-trioxabicyclo[2.2.2]octanes, " D. S. Milbrath, J. L. Engel, J. G. Verkade and J. E. Casida, Toxicology and Applied Pharmacology, 47, 287–293 (1979); "Structure-Toxicity Relationships of 2,6,7-Trioxabicyclo[2.2.2]octanes and Related Compounds," J. E. Casida, M. Eto, A. D. Moscioni, J. L. Engel, D. S. Milbrath and J. G. Verkade, Toxicology and Applied Pharmacology, 36, 261–279 (1976); "Nuclear Magnetic Resonance in Polycyclic Compounds. II. Long-Range H[1]-H[1] and H[1]-P[31] Coupling in Some Adamantane and Bicyclo[2.2.2]octane Derivatives," E. J. Boros, K. J. Coskran, R. W. King and J. G. Verkade, JACS, 88, 1140–1143 (1966); "Unusual Behavior of Hexafluorobenzene and Benzene in the Aromatic Nuclear Magnetic Resonance Shift Effect," R. D. Bertrand, R. D. Compton and J. G. Verkade, JACS, 92, 2702–2709 (1970); "A New General Synthetic Route to Bridged Carboxylic Ortho Esters," E. J. Corey and N. Raju, Tetrahedron Letters, 24, 5571–5574 (1983); and "Bicyclo Ortho Esters by Direct Esterification," R. A. Barnes, G. Doyle, and J. A. Hoffman, J. Org. Chem., 27, 90–93 (1962).

Intermediates for these reactions are described by "Ketene Acetals. XXXIV. Tetra- and Pentamethylene Ketene Acetals," S. M. McElvain and R. E. Starn, Jr., JACS, 77, 4571–4577 (1955); "Preparation of Trimethylolisobutane by Condensation of Isovaleraldehyde with Formaldehyde," M. M. Ketslakh, D. M. Rudkovskii, and F. A. Eppel, Oksosintez, Poluchenie Metodom Oksosinteza Al'degidov, Spritov i Vtorichnykh Produktov na ikh Osnove, Vses. Nauchn.-Issled., Inst. Neftekhim Protsessov (1963), 156–163; "Extensions of Tollens Condensation," O. C. Dermer and P. W. Solomon, JACS, 76, 1697–1699 (1954); and "Cyclic Ethers Made by Pyrolysis of Carbonate Esters", D. B. Pattison, JACS, 79, 3455–3456 (1957).

Three specific methods (A-C) were used to prepare the trioxabicyclooctanes (Table 6). Each procedure started from a triol synthesized from

TABLE 6

Characterization Data of 1,4-bis-Substituted-2,6,7-trioxabicyclo[2.2.2]octanes

| No. | X | R | Proc. of Syn.* | $^1$H nmr[a] δ | mp or bp (°C.)[b] | [M + 1]+c |
|---|---|---|---|---|---|---|
| 1 | 4-ClPh | Et | A | 0.85[3H, t, CH$_3$], 1.3[2H, q, CH$_2$], 4.05[6H, s, (CH$_2$O)$_3$], 7.3[2H, d, aromatic], 7.5[2H, d, aromatic] | 91–93 | |
| 2 | 4-ClPh | n-Pr | A | 0.9[3H, t, CH$_3$], 1.2–1.4[4H, m, CH$_2$CH$_2$], 4.15[6H, s, (CH$_2$O)$_3$], 7.4[2H, d, aromatic], 7.6[2H, d, aromatic] | 129–131 | 269 |
| 3 | 4-ClPh | i-Pr | A | 0.95[6H, d, (CH$_3$)$_2$C], 1.6[1H, m, CH], 4.15[6H, s, (CH$_2$O)$_3$], 7.3[2H, d, aromatic], 7.5[2H, d, aromatic] | 114–116 | 269 |
| 4 | 4-ClPh | n-Bu | A | 0.95[3H, t, CH$_3$], 1.2–1.5[6H, m, (CH$_2$)$_3$], 4.15[6H, s, (CH$_2$O)$_3$], 7.4[2H, d, aromatic], 7.6[2H, d, aromatic] | 111–114 | 283 |
| 5 | 4-ClPh | s-Bu | A | 0.85[3H, d, CH$_3$], 0.9[3H, t, CH$_3$], 1.2–1.6[3H, m, CH$_2$CH], 4.1[6H, s, (CH$_2$O)$_3$], 7.3 and 7.5[4H, 2xd, aromatic] | 119–120 | |
| 6 | 4-ClPh | t-Bu | A | 0.9[9H, s, (CH$_3$)$_3$C], 4.1[6H, s, (CH$_2$O)$_3$], 7.3 and 7.5[4H, 2xd, aromatic] | 176–178 | 283 |
| 7 | 4-ClPh | c-Pen | A | 1.1–1.75[9H, m, (CH$_2$)$_4$CH], 4.15[6H, s, (CH$_2$O)$_3$], 7.3 and 7.5[4H, 2xd, aromatic] | 170–173 | |
| 8 | 4-ClPh | c-Hex | A | 0.9–2.0[11H, m, (CH$_2$)$_5$CH], 4.15[6H, s, (CH$_2$O)$_3$], 7.4 and 7.65[4H, 2xd, aromatic] | 215–218 | 309 |
| 9 | 4-ClPh | Ph | A | 4.55[6H, s, (CH$_2$O)$_3$], 7.2–7.9[9H, m, aromatic] | 239–240 | |
| 10 | 4-ClPh | 4-MePh | A | 2.3[3H, s, CH$_3$], 4.45[6H, s, (CH$_2$O)$_3$], 7.0–7.7[8H, m, aromatic] | 254–256 | 317 |
| 11 | 4-ClPh | NO$_2$ | A | 3.95[6H, s, (CH$_2$O)$_3$], 7.45, 8.0[4H, 2xd, aromatic] | 23–24 | 272 |
| 12 | c-Hex | Et | A | 0.85[3H, t, CH$_3$], 1.0–2.0[13H, m, (CH$_2$)$_5$CH and CH$_2$], 3.95[6H, s, (CH$_2$O)$_3$] | 61–63 | 227 |
| 13 | c-Hex | c-Hex | A | 1.8–2.0[22H, m, (CH$_2$)$_5$CH and (CH$_2$)$_5$CH], 3.95[6H, s, (CH$_2$O)$_3$] | 240–242 | 281 |
| 14 | c-Hex | Ph | A | 0.9–1.9[11H, m, (CH$_2$)$_5$CH], 4.2[6H, s, | 195–196 | 275 |

TABLE 6-continued

Characterization Data of 1,4-bis-Substituted-2,6,7-trioxabicyclo[2.2.2]octanes

| No. | X | R | Proc. of Syn.* | $^1$H nmr$^a$ δ | mp or bp (°C.)$^b$ | [M + 1]+c |
|---|---|---|---|---|---|---|
| 15 | Ph | n-Pr | A | (CH$_2$O)$_3$], 7.0-7.4[5H, m, aromatic] 0.85[3H, t, CH$_3$], 1.0-1.3[4H, m, CH$_2$CH$_2$], 4.05[6H, s, (CH$_2$O)$_3$], 7.3-7.8[5H, m, aromatic] | 81-82 | |
| 16 | Ph | i-Pr | A,B | 0.9[6H, d, (CH$_3$)$_2$C], 1.6[1H, m, CH], 4.1[6H, s, (CH$_2$O)$_3$], 7.3-7.6[5H, m, aromatic] | 104-107 | 235 |
| 17 | Ph | t-Bu | A | 0.9[9H, s, (CH$_3$)$_3$C], 4.1[6H, s, (CH$_2$O)$_3$], 7.3-7.6[5H, m, aromatic] | 158-160 | 249 |
| 18 | Ph | c-Hex | A | 0.8-2.0[11H, m, (CH$_2$)$_5$CH], 4.15[6H, s, (CH$_2$O)$_3$], 7.3-7.8[5H, m, aromatic] | 181-183 | 275 |
| 19 | 2-FPh | t-Bu | A | 0.9[9H, s, (CH$_3$)$_3$C], 4.15[6H, s, (CH$_2$O)$_3$], 7.0-7.7[4H, m, aromatic] | 143-145 | 267 |
| 20 | 2-ClPh | t-Bu | B | 0.9[9H, s, (CH$_3$)$_3$C], 4.15[6H, s, (CH$_2$O)$_3$], 7.2-7.8[4H, m, aromatic] | 126-128 | |
| 21 | 3-ClPh | t-Bu | A | 0.9[9H, s, (CH$_3$)$_3$C], 4.15[6H, s, (CH$_2$O)$_3$], 7.2-7.6[4H, m, aromatic] | 163-166 | |
| 22 | 3-PhOPh | i-Pr | A | 0.9[6H, d, (CH$_3$)$_2$C], 1.6[1H, m, CH], 4.1[6H, s, (CH$_2$O)$_3$], 6.9-7.5[9H, m, aromatic] | 55-57 | |
| 23 | 4-FPh | t-Bu | A | 0.9[9H, s, (CH$_3$)$_3$C], 4.2[6H, s, (CH$_2$O)$_3$], 7.2-8.0[4H, m, aromatic] | 148-149 | 267 |
| 24 | 4-FPh | c-Hex | A | 0.9-2.0[11H, m, (CH$_2$)$_5$CH], 4.15[6H, s, (CH$_2$O)$_3$], 6.9-7.8[4H, m, aromatic] | 225-228 | 293 |
| 25 | 4-BrPh | t-Bu | A | 0.9[9H, s, (CH$_3$)$_3$C), 4.15[6H, s, (CH$_2$O)$_3$], 7.45[4H, s, aromatic] | 196-198 | |
| 26 | 4-BrPh | c-Hex | A | 0.9-1.9[11H, m, (CH$_2$)$_5$CH], 4.15[6H, s, (CH$_2$O)$_3$], 7.5(4H, s, aromatic] | 223-225 | |
| 27 | 4-CF$_3$Ph | t-Bu | A | 0.9[9H, (CH$_3$)$_3$C], 4.2[6H, s, (CH$_2$O)$_3$], 7.7[4H, q, aromatic] | 209-212 | |
| 28 | 4-NO$_2$Ph | i-Pr | B | 0.9[6H, d, (CH$_3$)$_2$C], 1.6[1H, s, CH], 4.15[6H, s, (CH$_2$O)$_3$], 7.75 and 8.2[4H, 2xd, aromatic] | 163-166 | 280 |
| 29 | 4-NO$_2$Ph | t-Bu | B | 0.9[9H, s, (CH$_3$)$_3$C], 4.2[6H, s, (CH$_2$O)$_3$], 7.75[2H, d, aromatic], 8.2[2H, d, aromatic] | 222-223 | |
| 30 | 4-CNPh | t-Bu | B | 0.9[9H, s, (CH$_3$)$_3$C], 4.2[6H, s, (CH$_2$O)$_3$], 7.65[4H, q, aromatic] | 207-208 | 274 |
| 31 | 4-CNPh | c-Hex | B | 0.95-1.8[11H, m, (CH$_2$)$_5$CH[, 4.1[6H, s, (CH$_2$O)$_3$], 7.55-7.75[4H, q, aromatic] | 239-241 | |
| 32 | 4-N$_3$Ph | t-Bu | B | 0.9[9H, s, (CH$_3$)$_3$C], 4.15[6H, s, (CH$_2$O)$_3$], 7.0 and 7.6[4H, 2xd, aromatic] | 122-124 | 290 |
| 33 | 4-MeSO$_2$Ph | n-Pr | B$^d$ | 0.9[3H, t, CH$_3$C], 1.2-1.3[4H, m, CH$_2$CH$_2$], 3.0[3H, s, CH$_3$SO$_2$], 4.1[6H, s, (CH$_2$O)$_3$], 7.8-7.9[4H, q, aromatic] | 218-221 | |
| 34 | 4-MeSPh | n-Pr | B | 0.9[3H, t, CH$_3$C], 1.2-1.3[4H, m, CH$_2$CH$_2$], 2.4[3H, s, CH$_3$S], 4.1[6H, s, (CH$_2$O)$_3$], 7.2 and 7.5[4H, 2xd, aromatic] | 74-76 | |
| 35 | 4-MeOPh | i-Pr | B | 0.9[6H, d, (CH$_3$)$_2$C], 1.6[1H, m, CH], 3.8[3H, s, OCH$_3$], 4.1[6H, s, (CH$_2$O)$_3$], 6.8 and 7.5[4H, 2xd, aromatic] | 83-85 | |
| 36 | 4-MePh | i-Pr | B | 0.9[6H, d, (CH$_3$)$_2$C], 1.6[1H, m, CH], 2.3[3H, s, CH$_3$], 4.1[6H, s, (CH$_2$O)$_3$], 7.1 and 7.5[4H, 2xd, aromatic] | 149-152 | |
| 37 | 4-t-BuPh | t-Bu | A | 0.9[9H, s, (CH$_3$)$_3$C], 1.3[9H, s, (CH$_3$)$_3$C], 4.2[6H, s, (CH$_2$O)$_3$], 7.6[4H, q, aromatic] | 224-225 | 305 |
| 38 | 3,4-Cl$_2$Ph | t-Bu | A | 0.9[9H, s, (CH$_3$)$_3$C], 4.1[6H, s, (CH$_2$O)$_3$], 7.35-7.7[3H, m, aromatic] | 170-172 | 317 |
| 39 | 3,4-Cl$_2$Ph | c-Hex | A | 0.9-1.8[11H, m, (CH$_2$)$_5$CH], 4.1[6H, s, (CH$_2$O)$_3$], 7.35-7.7[3H, m, aromatic] | 192-195 | |
| 40 | 3-NO$_2$, 4-ClPh | n-Pr | B | 0.9[3H, t, CH$_3$C], 1.2-1.3[4H, m, CH$_2$CH$_2$], 4.1[6H, s, (CH$_2$O)$_3$], 7.5-8.1[3H, m, aromatic] | 79-82 | |
| 41 | 3,4-OCH$_2$OPh | n-Pr | B | 0.9[3H, t, CH$_3$C], 1.2-1.3[4H, m, CH$_2$CH$_2$], 4.05[6H, s, (CH$_2$O)$_3$], 5.9[2H, s, OCH$_2$O], 6.7-7.1[3H, m, aromatic] | 108-110 | |
| 42 | F$_5$Ph | i-Pr | B | 0.9[6H, d, (CH$_3$)$_2$C], 1.6[1H, m, CH], 4.1[6H, s, (CH$_2$O)$_3$] | 109-110 | |
| 43 | F$_5$Ph | t-Bu | B | 0.9[9H, s, (CH$_3$)$_3$C], 4.15[6H, s, (CH$_2$O)$_3$] | 163-165 | 339 |
| 44 | Ph | Ph | A | 4.6[6H, s, (CH$_2$O)$_3$], 7.2-7.9[10H, m, aromatic] | 66-68 | 269 |
| 45 | 4-FPh | Ph | A | 4.5[6H, s, (CH$_2$O)$_3$], 6.9-7.8[9H, m, aromatic] | 188-192 | 287 |
| 46 | H | t-Bu | A | 0.85[9H, s, (CH$_3$)$_3$C], 4.0[6H, s, (CH$_2$O)$_3$], 5.5[1H, s, CH] | 84-86 | 173 |
| 47 | Me | t-Bu | A | 0.85[9H, s, (CH$_3$)$_3$C], 1.45[3H, s, CH$_3$], 4.0[6H, s, (CH$_2$O)$_3$] | 88-89 | 187 |
| 48 | Et | t-Bu | A | 0.85[9H, s, (CH$_3$)$_3$C], 0.95[3H, t, CH$_3$], 1.7[2H, q, CH$_2$], 4.0[6H, s, (CH$_2$O)$_3$] | 38-40 | 201 |

TABLE 6-continued

Characterization Data of 1,4-bis-Substituted-2,6,7-trioxabicyclo[2.2.2]octanes

| No. | X | R | Proc. of Syn.* | $^1$H nmr$^a$ δ | mp or bp (°C.)$^b$ | [M + 1]+$^c$ |
|---|---|---|---|---|---|---|
| 49 | n-Pr | t-Bu | A | 0.85[9H, s, (CH$_3$)$_3$C], 0.85[3H, t, CH$_3$], 1.2–1.8[4H, m, CH$_2$CH$_2$], 4.0[6H, s, (CH$_2$O)$_3$] | 57–60 | 215 |
| 50 | i-Pr | t-Bu | A | 0.9[9H, s, (CH$_3$)$_3$C], 1.0[6H, d, (CH$_3$)$_2$C], 1.8[1H, m, CH], 4.05[6H, s, (CH$_2$O)$_3$] | 81–83 | 215 |
| 51 | n-Bu | t-Bu | A | 0.9[9H, s, (CH$_3$)$_3$C], 0.9[3h, t, CH$_3$], 1.1–1.9[6H, m, (CH$_2$)$_3$], 4.0[6H, s, (CH$_2$O)$_3$] | 37–38 | 229 |
| 52 | s-Bu | i-Pr | C | 0.85[6H, d, (CH$_3$)$_2$C], 0.9[3H, t, CH$_3$], 0.9[3H, d, CH$_3$], 1.4–1.8[4H, m, CH$_2$CH and CH], 3.9[6H, s, (CH$_2$O)$_3$] | 87–90$^{0.5}$ | 215 |
| 53 | n-Pen | t-Bu | B | 0.8[9H, s, (CH$_3$)$_3$C], 0.85[3H, t, CH$_3$], 1.1–1.7[8H, m, (CH$_2$)$_4$], 3.9[6H, s, (CH$_2$O$_3$] | 29–30 | |
| 54 | neo-Pen | i-Pr | B | 0.8[6H, d, (CH$_3$)$_2$C], 0.9[9H, s, (CH$_3$)$_3$C], 1.5[1H, m, CH], 1.6[2H, s, CH$_2$], 3.9[6H, s, (CH$_2$O)$_3$] | 67–68 | |
| 55 | n-Hex | i-Pr | B | 0.8[6H, d, (CH$_3$)$_2$C], 0.85[3H, t, CH$_3$], 1.2–1.7[11H, (CH$_2$)$_5$ and CH], 3.9[6H, s, (CH$_2$O)$_3$] | 26–27 | |
| 56 | c-Pr | i-Pr | B | 0.4 and 0.55[4H, 2xm, CH$_2$CH$_2$], 0.8[6H, d, (CH$_3$)$_2$C], 1.1[1H, m, CH], 1.5[1H, m, CH], 3.9[6H, s, (CH$_2$O)$_3$] | 44–47 | |
| 57 | c-Bu | i-Pr | B | 0.85[6H, d, (CH$_3$)$_2$C], 1.5[1H, m, CH], 1.7–2.6[7H, m, (CH$_2$)$_3$CH], 3.9[6H, s, (CH$_2$O)$_3$] | 44–46 | |
| 58 | c-Pen | i-Pr | B | 0.95[6H, d, (CH$_3$)$_2$C], 1.5–1.9[10H, m, (CH$_2$)$_4$CH and CH], 4.05[6H, s, (CH$_2$O)$_3$] | 50–53 | |
| 59 | c-Hex | i-Pr | A | 0.85[6H, d, (CH$_3$)$_2$C], 1.0–2.0[12H, m, (CH$_2$)$_5$CH and CH], 4.0[6H, s, (CH$_2$O)$_3$] | 118–121 | 241 |
| 60 | c-Hex | t-Bu | A | 0.85[9H, s, (CH$_3$)$_3$C], 1.0–2.0[11H, m, (CH$_2$)$_5$CH], 4.0[6H, s, (CH$_2$O)$_3$] | 154–155 | 255 |
| 61 | c-Hept | i-Pr | B | 0.85[6H, d, (CH$_3$)$_2$C], 1.2–2.0[14H, m, (CH$_2$)$_6$CH and CH], 3.9[6H, s, (CH$_2$O)$_3$] | 106–108 | |
| 62 | c-Hept | t-Bu | B | 0.85[9H, s, (CH$_3$)$_3$C], 1.2–1.9[13H, m, (CH$_2$)$_6$CH], 3.95[6H, s, (CH$_2$O)$_3$] | 178–181 | |
| 63 | Vinyl | i-Pr | A$^e$ | 0.9[6H, d, (CH$_3$)$_2$C], 1.6[1H, m, CH], 4.15[6H, s, (CH$_2$O)$_3$], 5.3–6.0[3H, m, CH=CH$_2$] | liquid | |
| 64 | Ethynyl | i-Pr | A$^e$ | 0.9[6H, d, (CH$_3$)$_2$C], 1.6[1H, m, CH], 2.6[1H, s, C≡CH], 4.15[6H, s, (CH$_2$O)$_3$] | 144–147 | |
| 65 | Ethynyl | t-Bu | A$^e$ | 0.85[9H, s, (CH$_3$)$_3$C], 2.5[1H, s, C≡CH], 4.05[6H, s, (CH$_2$O)$_3$] | 195–197 | 197 |
| 66 | 1-BrEt | i-Pr | A | 0.9[6H, d, (CH$_3$)$_2$C], 1.6[1H, m, CH], 1.7]3H, d, CH$_3$CBr], 4.1[1H, m, CHBr], 4.15[6H, s, (CH$_2$O)$_3$] | liquid | |
| 67 | 1,2-Br$_2$Et | i-Pr | A$^e$ | 0.9[6H, d, (CH$_3$)$_2$C], 1.6[1H, m, CH], 3.65[2H, m, CH$_2$Br], 4.1[6H, s, (CH$_2$O)$_3$], 4.25[1H, m, CHBr] | liquid | |
| 68 | Benzyl | t-Bu | A | 0.8[9H, s, (CH$_3$)$_3$C], 3.0[2H, s, CH$_2$], 4.0[6H, s, (CH$_2$O)$_3$], 7.2–7.4[5H, m, aromatic] | 98–100 | 263 |
| 69 | n-Bu | n-Pr | A | 0.9[6H, 2xt, 2xCH$_3$], 1.1–1.7[10H, m, (CH$_2$)$_3$ and (CH$_2$)$_2$], 3.9[6H, s, (CH$_2$O)$_3$] | 74–75$^{0.7}$ | 215 |
| 70 | 1-Bicyclo-[2.2.1]heptyl | n-Pr | B | 0.9[3H, t, CH$_3$], 1.1–2.2[15H, m, 7 × CH$_2$ and CH], 3.9[6H, s, (CH$_2$O)$_3$] | 118–121 | |
| 71 | 2-Bicyclo-[2.2.1]heptyl | n-Pr | B | 0.9[3H, t, CH$_3$], 1.05–2.3[15H, m, 6 × CH$_2$ and 3 × CH], 3.9[6H, s, (CH$_2$O)$_3$] | 80–82 | |
| 72 | Cyclohex-3-enyl | n-Pr | B | 0.9[3H, t, CH$_3$], 1.1–1.2]4H, m, CH$_2$CH$_2$], 1.7–2.2[6H, m, (CH$_2$)$_3$], 3.9[6H, s, (CH$_2$O)$_3$], 5.6[2H, m, CH=CH] | 55–57 | |
| 73 | 5-Bromo-2-furyl | n-Pr | B | 0.9[3H, t, CH$_3$], 1.2–1.3[4H, m, CH$_2$CH$_2$], 4.1[6H, s, (CH$_2$O)$_3$], 6.25 and 6.45[2H, 2 × d, CH=CH] | 73–75 | |
| 74 | c-Hept | c-Hex | B | 0.85–1.95[24H, m, (CH$_2$)$_6$CH and (CH$_2$)$_5$CH], 3.9[6H, s, (CH$_2$O)$_3$] | 188–190 | |

$^a$Spectra obtained at 90 or 300 MHz for samples dissolved in deuterochloroform. Integrations were consistent with structural assignments.
$^b$Superscript indicates pressures (mm Hg) at which bp was measured, lack of superscript indicates mp.
$^c$Quasi-molecular ion obtained with chemical ionization at 230 eV with methane (0.8 Torr).
$^d$Sulfone 33 was obtained from thioether 34 on oxidation with two equivalents of 3-chloroperoxybenzoic acid in dichloromethane.
$^e$1-BrEt compound 66 was subjected to sequential dehydrobromination, bromination and dehydrobromination to obtain vinyl derivative 63, 1,2-Br$_2$Et compound 67 and ultimately the ethynyl derivative 64. A similar procedure was used to prepare ethynyl derivative 65.
*Procedures of synthesis as specified in the text.

the corresponding substituted-acetaldehyde by hydroxymethylation and subsequent crossed-Cannizzaro reaction (Dermer and Solomon, 1954; Ketslakh et al., 1963). The reaction scheme was:

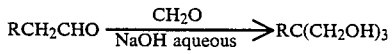

Each trioxabicyclooctane gave appropriate proton nuclear magnetic resonance (NMR) and mass spectrometry (MS) characteristics (Table 6). Abbreviations used in NMR data are s=singlet, d=doublet, 2xd=two doublets, dd=doublet of doublets, t=triplet, 2xt=two triplets, q=quartet and m=multiplet.

PROCEDURE A.

Acid-catalyzed Condensation of a Triol with an Orthocarboxylate (Boros et al., 1966; Bertrand et al., 1970)

The equation for the reaction being:

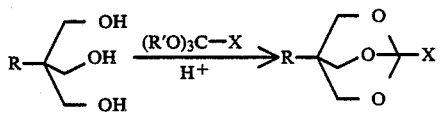

where R' may be alkyl or aryl, preferably methyl or ethyl. For example, a mixture of 2-t-butyl-2-hydroxymethyl-1,3-propanediol (R=t—Bu) (0.4 g, 2.5 mmol), trimethyl orthocyclohexanecarboxylate (X=c—Hex; R'=CH$_3$), (0.5 g, 2.5 mmol) and 4-toluenesulphonic acid (10 mg) was heated to 160° C. until methanol distilled over. The residue was vacuum dried (at 1 mm Hg) and then passed down a short basic alumina column to give trioxabicyclooctane 60 (X=c—Hex; R=t—Bu) (0.6 g, 95%). Directly analogous procedures were used to prepare compounds 1-19, 21-27, 37-39, 44-51, 59 and 63-69.

Intermediate trimethyl orthocarboxylates were commercially available or were synthesized by either of two procedures illustrated with the methyl esters. In the first procedure, the appropriate benzotrichloride or benzotribromide (from bromination of the corresponding toluene with N-bromosuccinimide (NBS)) was subjected to halide displacement with methoxide (McElvain and Venerable, 1950). These methods were as follows:

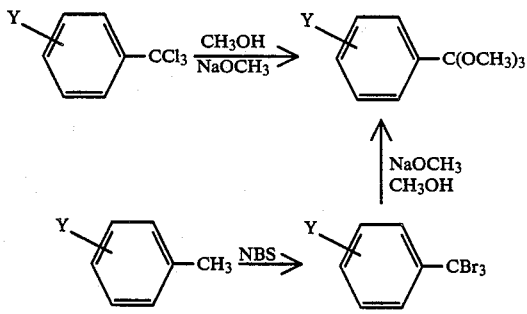

wherein Y represents hydrogen or one or more other groups such as halo or trifluoromethyl.

In the second procedure, the appropriate nitrile was treated with methanol and hydrochloric acid to obtain the imino ester hydrochloride and ultimately the trimethyl orthocarboxylate (McElvain and Starn, 1955). This procedure was as follows:

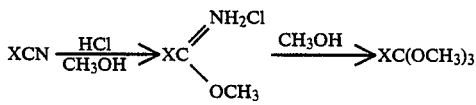

PROCEDURE B

Rearrangement of an Acylated Hydroxymethyloxetane (Corey and Raju, 1983)

Acylation of 3-substituted -3-hydroxymethyloxetanes (prepared from the appropriate triol via pyrolysis of the carbonate ester) (Pattison, 1957) gives the corresponding oxetane esters which can be rearranged in the presence of boron trifluoride etherate to form trioxabicyclooctanes. The equation for the reaction being:

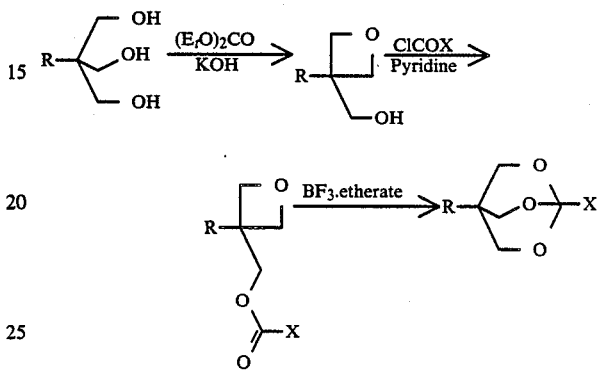

For example, 4-nitrobenzoyl chloride (2.28 g, 12.3 mmol) in dry dichloromethane (4 ml) was added to 3-isopropyl-3-hydroxymethyloxetane (1.6 g, 12.3 mmol) in dry dichloromethane (15 ml) and dry pyridine (2 ml) at 0° C. under a nitrogen atmosphere. The solution was stirred overnight, then extracted with water, dried (sodium sulfate), filtered and evaporated to leave the 4-nitrobenzoyl ester (3.4 g, 99%) as a residue which was not purified further. $^1$H NMR (CDCl$_3$), δ1.0 [6H, d, (CH$_3$)$_2$C], 2.3 [1H, m, C—CH], 4.55 [2H, s, CH$_2$OCO], 4.6 [4H, dd, CH$_2$OCH$_2$], 8.3 [4H, q, aromatic]. This residue was dissolved in dry dichloromethane (15 ml) under a nitrogen atmosphere, cooled to −55° C. and boron trifluoride etherate (2 ml) was added. The mixture was allowed to warm to room temperature an was then quenched with triethylamine, evaporated to dryness and partitioned between dichoromethane and water. The organic layer was separated, dried (potassium carbonate) and evaporated. The residue was purified by passage through a short basic alumina column to afford trioxabicyclooctane 28 (X=4—NO$_2$Ph; R=i—Pr) (1.7 g, 50%). Directly analogous procedures were used to prepare compounds 16, 20, 29-36, 40-43, 53-58, 61, 62 and 70-74.

PROCEDURE C

Acid-catalyzed Condensation of a Triol Directly with a Carboxylic Acid, Acid Chloride, or the like (Barnes et al., 1962)

The equation for the reaction being:

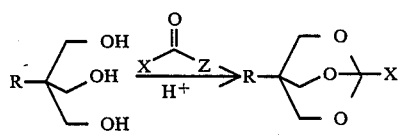

wherein Z represents hydroxyl, halo, acyl, cyano, or other group which it is suitable and customary to use in condensation reactions. Thus, a solution of 2-isopropyl- 2-hydroxymethyl-1,3-propanediol (3 g, 20 mmol), 2-methylbutyric acid (2 g, 20 mmol) and 4-toluenesulphonic acid (20 mg) in benzene (100 ml) was heated to reflux for 12 hours and the water formed was separated off. The solution was evaporated down to low volume and then distilled under reduced pressure to give trioxabicyclooctane 52 (X=s—Bu; R=i—Pr) (2.55 g, 62%).

BIOLOGICAL ACTIVITY DETERMINATION

EXAMPLE 1

$LD_{50}$ for *Musca domestica*

The compounds listed in Tables 1–4 were tested for insecticidal activity by dissolving them in acetone or in tetrahydofuran if they were insoluble in acetone. Subsequent dilutions were prepared using the same solvent. The compound solutions (0.5 microliter) were applied topically to the ventrum of the abdomen of anesthetized adult female houseflies (*Musca domestica* L., SCR strain, 3–5 days after emergence, 20 mg each). The toxicity studies were varied by treating the houseflies topically with PB at 250 micrograms per gram, two to three hours prior to administering the toxicant. The treated houseflies were provided sugar and water, and mortality was determined after 24 hours at 25° C. The data in Tables 1–4 are reported as the lethal dose, in micrograms of toxicant per gram of insect weight required to kill 50% of the fly population and are referred to as the $LD_{50}$ values.

Tables 1–4 give the structure-activity relationships for the test compounds on houseflies and on houseflies pre-treated with PB. Many of the compounds are active in the same potency range in this test as current commercial pesticides. The compounds at present tested contain the following R and X substituents:

R=ethyl, n-propyl, iso-propyl, n-butyl, s-butyl, tert-butyl, cyclopentyl, cyclohexyl, phenyl, 4-methylphenyl and nitro X=hydrogen, methyl, ethyl, vinyl, ethynyl, 1-bromoethyl, 1,2-dibromoethyl, n-propyl, iso-propyl, cyclopropyl, n-butyl, s-butyl, cyclobutyl, n-pentyl, neopentyl, cyclopentyl, n-hexyl, cyclohexyl, cycloheptyl, cyclohex-3-enyl, 1-bicyclo[2.2.1]heptyl, 2-bicyclo[2.2.1]heptyl, 5-bromo-2-furyl, phenyl, 2-chlorophenyl, 3-chlorophenyl, 4-chlorophenyl, 2-fluorophenyl, 4-fluorophenyl, 4-bromophenyl, 3,4-dichlorophenyl, benzyl, 4-tert-butylphenyl, 3-phenoxyphenyl, 4-trifluoromethylphenyl, 4-azidophenyl, 4-nitrophenyl, 4-cyanophenyl, 4-methylsulfonylphenyl, 4-methylthiophenyl, 4-methoxyphenyl, 4-methylphenyl, 4-chloro-3-nitrophenyl, 3,4-methylenedioxyphenyl, and 2,3,4,5,6-pentafluorophenyl.

Combinations of the following R and X groups tended to provide compounds having insecticidal activity against *Musca domestica*:

R=ethyl, n-propyl, iso-propyl, n-butyl, s-butyl, tert-butyl, cyclopentyl, cyclohexyl or phenyl; and X=vinyl, ethynyl, 1-bromoethyl, n-butyl, 1,2-dibromoethyl, cyclopropyl, s-butyl, n-propyl, n-pentyl, cyclobutyl, neo-pentyl, cyclopentyl, n-hexyl, cyclohexyl, cycloheptyl, cyclohex-3-enyl, 1-bicyclo[2.2.1]heptyl, 2-bicyclo[2.2.1]heptyl, 5-bromo-2-furyl, 2-chlorophenyl, 3-chlorophenyl, 4-chlorophenyl, 2-fluorophenyl, 4-fluorophenyl, 4-bromophenyl, 3,4-dichlorophenyl, phenyl, 3-phenoxyphenyl, 4-trifluoromethylphenyl, 4-azidophenyl, 4-nitrophenyl, 4-cyanophenyl, benzyl, 4-methylsulfonylphenyl, 4-methylthiophenyl, 4-methoxyphenyl, 4-methylphenyl, 4-chloro-3-nitrophenyl, 3,4-methylenedioxyphenyl or 2,3,4,5,6-pentafluorophenyl.

Significant insecticidal activity against the common housefly was found with suitable combinations of the following R and X substituents:

R=n-propyl, iso-propyl, n-butyl, s-butyl, tert-butyl, cyclopentyl, cyclohexyl, or phenyl; and X=n-butyl, n-pentyl, cyclohexyl, cycloheptyl, 4-cyanophenyl, 3,4-dichlorophenyl, 3-chlorophenyl, 4-chlorophenyl, 4-bromophenyl, 4-fluorophenyl, 4-nitrophenyl, 4-azidophenyl, pentafluorophenyl, 2-bicyclo[2.2.1]heptyl, phenyl, 2-fluorophenyl, 4-trifluoromethylphenyl, n-hexyl, ethynyl, 1-bicyclo[2.2.1]heptyl, 5-bromo-2-furyl, or cyclohex-3-enyl.

Particularly preferred compounds are those obtained from any of the combinations resulting when:

R=n-propyl, iso-propyl, n-butyl, s-butyl, tert-butyl, cyclopentyl, cyclohexyl, or phenyl; and X=n-butyl, n-pentyl, cyclohexyl, cycloheptyl, 4-cyanophenyl, 3,4-dichlorophenyl, 3-chlorophenyl, 4-chlorophenyl, 4-bromophenyl, 4-fluorophenyl, 4-nitrophenyl, 4-azidophenyl, pentafluorophenyl, 2-bicyclo[2.2.1]hetpyl, or cyclohex-3-enyl.

Compounds may also be active when the 1-phenyl moiety (X) is substituted in any one of the 3,4 or 5 positions by a group with a positive Hammett's sigma value, this value referring to the electronic property of a substituent (C. Hansch and A. Leo, "Substituent Constants for Correlation Analysis in Chemistry and Biology," John Wiley and Sons, New York, 1979)). Such groups include but are not restricted to: Br, $CCl_3$, $CF_3$, CN, CHO, $CH_2Br$, $CH_2Cl$, $CH_2I$, $CONH_2$, CH=NOH, C=O($CF_3$), 3,4-($CF_2OCF_2$), C≡CH, $CH_2SCF_3$, $CH_2SO_2CF_3$, $COCH_3$, $CO_2CH_3$, C≡$CCF_3$, CF($CF_3$)$_2$, CH=$CHCF_3$, C≡$CCH_3$, $CO_2C_2H_5$, $CF_2CF_2CF_2CF_3$, 2-thienyl, $C_6Cl_5$, $C_6F_5$, 2benzoxazolyl, 2-benzthiazolyl, C=O($C_6H_5$), CH=$NC_6H_5$, C≡$CC_6H_5$, Cl, F, I, $NO_2$, NNN, 5-Cl-l-tetrazolyl, 1-tetrazolyl, $NHCSNH_2$, $NHCOCF_3$, 3,4-($OCF_2O$), $OCF_3$, $OCHF_2$, $OCF_2CHFCl$, $OCOCH_3$, PO($OCH_3$)$_2$, PO($OC_2H_5$)$_2$, PO($OC_3H_7$)$_2$, $SO_2(NH_2)$, SCN, $OCF_2CF_2H$, $COCH_2CH_3$, $COCH(CH_3)_2$, $COC(CH_3)_3$, CH=C(CN)$_2$ and $COOC_6H_5$.

Other X or R substituents which may confer activity are substituted-cycloalkanes or cycloalkenes or heterocycles of 5 to 10 carbon atoms. R may also confer activity when it is a substituted-phenyl or heterocyclic group.

Compounds having pesticidal activity include those wherein R is a normal or branched propyl or butyl, or phenyl or cycloalkyl having 3 to 10 carbon atoms and X is cycloalkyl or cycloalkenyl having 6 to 10 carbon atoms, or substituted phenyl. Another group of compounds with demonstrated pesticidal activity are those where R is normal or branched propyl or butyl, phenyl or cycloalkyl having 5 or 6 carbon atoms and X is cyclohexyl, cycloheptyl, cyclohexenyl, ethynyl, or substituted phenyl. Yet another group of active compounds are those wherein R is n-propyl, normal or branched butyl, cyclopentyl or cyclohexyl and X is cyclohexyl, cycloheptyl or phenyl substituted in the 3- and/or 4-position by substituents independently selected from halo, cyano, azido and nitro provided that the substituted phenyl is not 4-chloro-3-nitrophenyl. Still another group of active compounds are those wherein R is phenyl and X is phenyl substituted in the 3- and/or 4-positions with chloro and/or bromo.

Compounds which have been prepared and tested for insecticidal activity and which exhibit very high activity (generally an LD$_{50}$ for *Musca domestica* of less than or equal to about 5.5 μg/g when used along with PB) include those wherein:

X is 4-chlorophenyl and R is n-propyl, n-butyl, s-butyl, t-butyl, cyclopentyl, cyclohexyl or phenyl;

R is t-butyl and X is cyclohexyl, cycloheptyl, 4-fluorophenyl, 4-bromophenyl, 4-nitrophenyl, 4-cyanophenyl or 3,4-dichlorophenyl; and R is cyclohexyl an X is cyclohexyl, cycloheptyl, 4-fluorophenyl, 4-bromophenyl, 4-cyanophenyl or 3,4-dichlorophenyl.

On a more general basis, R and X can be substantially any organic substituents, so long as the required activity is found. To date, activity has been found where R and X are n-alkyl, branched-alkyl, alkenyl, alkynyl, cycloalkyl, substituted-cycloalkyl, phenyl, substituted phenyl or heterocyclic substituents. While not all compounds with these substituents are active, many suitable combinations exist. Furthermore, simple tests as set out above with houseflies, or similar tests run with any desired pest, quickly determine which combinations are suitable for use against any particular pest.

EXAMPLE 2

Tests with Other Insects

The compounds listed in Table 5 were tested for toxicity to adult male American cockroaches (*Periplaneta americana*) by applying test solutions, as in Example 1, to the thorax using 1.0 μl carrier solvent per insect. In each case the cockroaches were also tested after topical pretreatment with PB at 250 μg/g 2 hours before administering the trioxabicyclooctane. LD$_{50}$ values were established after 24 hours at 25° C. The compounds tested are strongly synergized by PB to achieve a potency similar to that compound with PB-treated houseflies except for two compounds (13 and 38) which are >10-fold more toxic to houseflies than to cockroaches. Other tests showed that compound 6 was also toxic to the mosquito larva, black bean aphid, German cockroach and milkweed bug. Thus, the wide range of usefulness of the new class of pesticides set forth herein has been established.

EXAMPLE 3

Tests with Other Synergists

Other synergists known to serve as inhibitors of oxidative detoxification can be used in place of PB. This has been confirmed with tests on houseflies with the compound wherein R is tert-butyl and X is 4-chlorophenyl. The synergism factor achieved with PB at 250 micrograms per gram is also achieved when this synergist is replaced with either O-phenyl(2-methylpropyl) O-(2-propynyl) phenylphosphonate at 125 micrograms per gram or O,O-diethyl O-phenyl phosphorothioate at 50 micrograms per gram. In these tests the synergist and insecticide were applied at the same time to more closely simulate actual use situations. These synergists are relatively low in cost and mammalian toxicity. Many compounds are therefore useful and of economic benefit as synergists in improving the insecticidal activity of insecticidal trioxabicyclooctanes.

EXAMPLE 4

Test of Mammalian Toxicity

The mammalian toxicities of two of the compounds of the present invention were determined by individually dissolving each compound in olive oil and administering each resulting solution intraperitoneally to mice for determination of the mortality 24 hours later. The compounds were: R is tert-butyl and X is cyclohexyl (60); R is isopropyl and X is cyclohexyl (59). The injected $LD_{50}$ values for the tert-butyl and iso-propyl compounds are greater than 200 and 500 milligrams per kilogram body weight, respectively.

As is apparent, some compounds of the present invention have relatively low mammalian toxicity, specifically an injected $LD_{50}$ of greater than 200 milligrams of compound per kilogram of body weight. The mammalian toxicity may vary significantly depending upon the solvent carriers, routes of administration and species of mammal.

INDUSTRIAL APPLICABILITY

The compounds of the present invention show significant activity as pesticides against widely different types of insects. The compounds biodegrade readily.

We claim:

1. A pesticidal composition, comprising:

a compound having a formula $$R—C(CH_2O)_3C—X$$

wherein R and X are each organic substituents, said compound having the characteristic of exhibiting an $LD_{50}$ for pesticidal activity against *Musca domestica, Periplaneta americana,* the mosquito larvae, the black bean aphid, the German cockroach or the milkweed bug, in micrograms of compound per gram of body weight of *Musca domestica, Periplaneta americana,* the mosquito larvae, the black bean aphid, the German cockroach or the milkweed bug, of no more than about 400.

2. A pesticidal composition as set forth in claim 1, in combination with a synergist which functions to inhibit oxidative detoxification of said compound, the combination having the characteristic of exhibiting an $LD_{50}$ for pesticidal activity, in micrograms of compound per gram of body weight of *Musca domestica, Periplaneta americana,* the mosquito larvae, the black bean aphid, the German cockroach or the milkweed bug, of no more than about 20.

3. A pesticidal composition as set forth in claim 1, further including:

an inert carrier which serves as a diluent or vehicle for said compound.

4. A pesticidal composition as set forth in claim 1, wherein R is normal or branched alkyl, cycloalkyl or aryl and X is cycloalkyl, substituted cycloalkyl or substituted phenyl.

5. A pesticidal composition as set forth in claim 4, wherein R has three to ten carbon atoms and X has six to ten carbon atoms.

6. A pesticidal composition as set forth in claim 4, wherein X comprises cycloalkyl or substituted cycloalkyl having six to ten carbon atoms.

7. A pesticidal composition as set forth in claim 4, wherein X is substituted phenyl-and wherein the substituents on the phenyl are halo, cyano, nitro or azido groups.

8. A pesticidal composition, comprising:
a compound having a formula

R—C(CH$_2$O)$_3$C—X wherein R and X are each organic substituents; and
a synergist for improved pesticidal activity, said synergist functioning to inhibit oxidative detoxification of said compound.

9. A pesticidal composition as set forth in claim 8, further including:
an inert carrier which serves as a diluent or vehicle for said compounds.

10. A composition of matter, comprising:
a compound having a formula

R—C(CH$_2$O)$_3$ C—X wherein
R = n-propyl, iso-propyl, n-butyl, s-butyl, tert-butyl, cyclopentyl, cyclohexyl, phenyl, 4-methylphenyl or nitro; and wherein
X = vinyl, ethynyl, 1-bromoethyl, 1,2-dibromoethyl, cyclopropyl, s-butyl, cyclobutyl, neo-pentyl, cyclopentyl, n-hexyl, cyclohexyl, cycloheptyl, cyclohex-3-enyl, 1-bicyclo[2.2.1]heptyl, 2-bicyclo[2.2.1]heptyl, 5-bromo-2-furyl, 2-chlorophenyl, 3-chlorophenyl, 4-chlorophenyl, 2-fluorophenyl, 4-fluorophenyl, 4-bromophenyl, 3,4-dichlorophenyl, 4-tert-butylphenyl, 3-phenoxyphenyl, 4-trifluoromethylphenyl, 4-azidophenyl, 4-nitrophenyl, 4-cyanophenyl, 4-methylsulfonylphenyl, 4-methylthiophenyl, 4-methoxyphenyl, 4-methylphenyl, 4-chloro-3-nitrophenyl, 3,4-methylenedioxyphenyl or 2,3,4,5,6-pentafluorophenyl.

11. A composition of matter, comprising: a compound having a formula

R—C(CH$_2$O)$_3$C—X wherein:
X is 4-chlorophenyl and R is ethyl, n-propyl, i-propyl, n-butyl, s-butyl, t-butyl, cyclopentyl, cyclohexyl, phenyl, 4-methylphenyl, or nitro; or wherein
X is cyclohexyl and R is cyclohexyl, ethyl or phenyl; or wherein
R is cyclohexyl and X is phenyl, 4-fluorophenyl, 4-bromophenyl, 4-cyanophenyl, 3,4-dichlorophenyl, or cycloheptyl; or wherein
R is t-butyl and X is 2-fluorophenyl, 2-chlorophenyl, 3-chlorophenyl, 4-fluorophenyl, 4-bromophenyl, 4-trifluoromethylphenyl, 4-nitrophenyl, 4-cyanophenyl, 4-azidophenyl, 4-t-butylphenyl, 3,4-dichlorophenyl, 2,3,4,5,6-pentafluorophenyl, n-pentyl, cyclohexyl, cycloheptyl, ethynyl, or benzyl; or wherein
R is i-propyl and X is 3-phenoxyphenyl, 4-nitrophenyl, 4-methoxyphenyl, 4-methylphenyl, 2,3,4,5,6-pentafluorophenyl, s-butyl, neopentyl, n-hexyl, cyclopropyl, cyclobutyl, cyclopentyl, cyclohexyl, cycloheptyl, vinyl, ethynyl, 1-bromoethyl or 1,2-dibromoethyl; or wherein
R is n-propyl and X is 4-methylsulfonylphenyl, 4-methylthiophenyl, 4-chloro-3nitrophenyl, 3,4-methylenedioxyphenyl, 1bicyclo[2.2.1]heptyl, 2-bicyclo[2.2.1]heptyl, cyclohex-3-enyl or 5-bromo-2-furyl; or wherein
R is phenyl and X is phenyl or 4-fluorophenyl.

12. A composition of matter as set forth in claim 11, wherein:
X is 4-chlorophenyl and R is n-propyl, n-butyl, s-butyl, t-butyl, cyclopentl, cyclohexyl or phenyl; or
R is t-butyl and X is cyclohexyl, cycloheptyl, 4-fluorophenyl, 4-bromophenyl, 4-nitrophenyl, 4-cyanophenyl or 3,4-dichlorophenyl; or
R is cyclohexyl and X is cyclohexyl, cycloheptyl, 4-fluorophenyl, 4-bromophenyl, 4-cyanophenyl or 3,4-dichlorophenyl.

13. A method of killing insects, nematodes, molluscs, acarines or parasites, comprising:
contacting said insects, nematodes, molluscs, acarines or parasites, with an effective amount for killing said insects, nematodes, molluscs, acarines or parasites of a pesticidal composition comprising a compound having a formula

R—C(CH$_2$O)$_3$C—X wherein R and X are each organic substituents.

14. A method as set forth in claim 13, further including:
contacting said insects with a synergist for pesticidal activity said synergist functioning to inhibit oxidative detoxification of said compound.

15. A method as set forth in claim 13, wherein:
R = ethyl, n-propyl, iso-propyl, n-butyl, s-butyl, tert-butyl, cyclopentyl, cyclohexyl or phenyl; and wherein
X = vinyl, ethynyl, 1-bromoethyl, n-butyl, 1,2-dibromoethyl, cyclopropyl, s-butyl, n-propyl, n-penytl, cyclobutyl, neo-pentyl, cyclopentyl, n-hexyl, cyclohexyl, cycloheptyl, cyclohex-3-enyl, 1bicyclo[2.2.1]heptyl, 2-bicyclo[2.2.1]heptyl, 5-bromo-2-furyl, 2-chlorophenyl, 3-chlorophenyl, 4-chlorophenyl, 2-fluorophenyl, 4-fluorophenyl, 4-bromophenyl, 3,4-dichlorophenyl, phenyl, 3-phenoxyphenyl, 4-trifluoromethylphenyl, 4-azidophenyl, 4-nitrophenyl, 4-cyanophenyl, benzyl, 4-methylsulfonylphenyl, 4-methylthiophenyl, 4-methoxyphenyl, 4-methylphenyl, 4-chloro-3-nitrophenyl, 3,4-methylenedioxyphenyl or 2,3,4,5,6-pentafluorophenyl.

16. A method as set forth in claim 13, wherein:
X is 4-chlorophenyl and R is ethyl, n-propyl, i-propyl, n-butyl, s-butyl, t-butyl, cyclopentyl, cyclohexyl, phenyl, 4-methylphenyl, or nitro; or wherein
X is cyclohexyl and R is cyclohexyl, ethyl or phenyl; or wherein
R is cyclohexyl and X is phenyl, 4-fluorophenyl, 4-bromophenyl, 4-cyanophenyl, 3,4-dichlorophenyl, or cycloheptyl; or wherein
R is t-butyl and X is 2-fluorophenyl, 2-chlorophenyl, 3-chlorophenyl, 4-fluorophenyl, 4-bromophenyl, 4-trifluoromethylphenyl, 4-nitrophenyl, 4-cyanophenyl, 4-azidophenyl, 4-t-butylphenyl, 3,4-dichlorophenyl, 2,3,4,5,6-pentafluorophenyl, n-pentyl, cyclohexyl, cycloheptyl, ethynyl, or benzyl; or wherein
R is i-propyl and X is 3-phenoxyphenyl, 4-nitrophenyl, 4-methoxyphenyl, 4-methylphenyl, 2,3,4,5,6-pentafluorophenyl, s-butyl, neopentyl, n-hexyl, cyclopropyl, cyclobutyl, cyclopentyl, cyclohexyl, cycloheptyl, vinyl, ethynyl, 1-bromoethyl or 1,2-dibromoethyl; or wherein R is n-propyl and X is 4-methylsulfonylphenyl, 4-methylthiophenyl, 4-chloro-3-nitrophenyl, 3,4-methylenedioxyphenyl, 1-bicyclo[2.2.1]heptyl, 2-bicyclo[2.2.1]heptyl, cyclohex-3-enyl or 5-bromo-2-furyl; or wherein R is phenyl and X is phenyl or 4-fluorophenyl.

17. A method as set forth in claim 13, wherein:

X is 4-chlorophenyl and R is n-propyl, n-butyl, s-butyl, t-butyl, cyclopentyl, cyclohexyl or phenyl; or R is t-butyl and X is cyclohexyl, cycloheptyl, 4-fluorophenyl, 4-bromophenyl, 4-nitrophenyl, 4-cyanophenyl or 3,4-dichlorophenyl; or R is cyclohexyl and X is cyclohexyl, cycloheptyl, 4-fluorophenyl, 4-bromophenyl, 4-cyanophenyl or 3,4-dichlorophenyl.

18. A method as set forth in claim 13, wherein:

R = n-propyl, iso-propyl, n-butyl, s-butyl, tert-butyl, cyclopentyl, cyclohexyl, or phenyl; and X = n-butyl, n-pentyl, cyclohexyl, cycloheptyl, 4-cyanophenyl, 3,4-dichlorophenyl, 3-chlorophenyl, 4-chlorophenyl, 4-bromophenyl, 4-fluorophenyl 4-nitrophenyl, 4-azidophenyl, 2,3,4,5,6-pentafluorophenyl, 2-bicyclo[2.2.1]heptyl, phenyl, 2-fluorophenyl, 4-trifluoromethylphenyl, n-hexyl, ethynyl, 1-bicyclo[2.2.1]heptyl, 5-bromo-2-furyl, or cyclohex-3-enyl.

19. A pesticidal composition as set forth in claim 1, wherein said pesticidal activity is insecticidal activity and is against *Musca domestica*.

20. A pestcidal composition as set forth in claim 8, wherein said pesticidal activity is insecticidal activity and is against *Musca domestica*.

* * * * *